US008679856B2

(12) United States Patent
Manaresi (10) Patent No.: US 8,679,856 B2
(45) Date of Patent: Mar. 25, 2014

(54) METHOD AND APPARATUS FOR THE PROCESSING AND/OR ANALYSIS AND/OR SELECTION OF PARTICLES, IN PARTICULAR BIOLOGICAL PARTICLES

(75) Inventor: Nicolò Manaresi, Bologna (IT)

(73) Assignee: Silicon Biosystems S.p.A., Bologna (IT)

( * ) Notice: Subject to any disclaimer, the term of this patent is extended or adjusted under 35 U.S.C. 154(b) by 482 days.

(21) Appl. No.: 12/294,860

(22) PCT Filed: Mar. 26, 2007

(86) PCT No.: PCT/IB2007/000751
§ 371 (c)(1),
(2), (4) Date: Sep. 26, 2008

(87) PCT Pub. No.: WO2007/110739
PCT Pub. Date: Oct. 4, 2007

(65) Prior Publication Data
US 2010/0248285 A1    Sep. 30, 2010

(30) Foreign Application Priority Data
Mar. 27, 2006   (IT) .............................. TO2006A0226

(51) Int. Cl.
*G01N 1/34* (2006.01)
(52) U.S. Cl.
USPC .............................. 436/175; 436/174; 436/52
(58) Field of Classification Search
USPC ............. 436/63, 52, 174, 175, 177, 178, 180;
210/695, 748.01, 748.02, 748.05, 767,
210/790
See application file for complete search history.

(56) References Cited

U.S. PATENT DOCUMENTS

| | | | |
|---|---|---|---|
| 5,252,493 A | 10/1993 | Fujiwara |
| 5,279,493 A | 1/1994 | Halder |
| 5,279,936 A | 1/1994 | Vorpahl |
| 5,888,370 A | 3/1999 | Becker et al. |
| 5,945,281 A | 8/1999 | Prabhu |
| 6,149,489 A | 11/2000 | Johnson |
| 6,149,789 A | 11/2000 | Benecke et al. |
| 6,203,683 B1 | 3/2001 | Austin et al. |
| 6,264,815 B1 | 7/2001 | Pethig et al. |
| 6,294,063 B1 | 9/2001 | Becker et al. |
| 6,824,664 B1 | 11/2004 | Austin et al. |
| 6,830,729 B1 | 12/2004 | Holl et al. |
| 6,875,329 B2 | 4/2005 | Washizu et al. |
| 6,888,721 B1 | 5/2005 | Moghaddam et al. |
| 6,911,132 B2 | 6/2005 | Pamula et al. |
| 6,977,033 B2 | 12/2005 | Becker et al. |
| 7,147,763 B2 | 12/2006 | Elrod et al. |
| 7,250,933 B2 | 7/2007 | De Boer et al. |
| 7,307,328 B2 | 12/2007 | Meyer et al. |
| 7,488,406 B2 | 2/2009 | Hughes et al. |
| 7,641,779 B2 | 1/2010 | Becker et al. |
| 8,216,513 B2 | 7/2012 | Becker et al. |
| 8,349,160 B2 | 1/2013 | Medoro et al. |
| 8,388,823 B2 | 3/2013 | Manaresi et al. |
| 2002/0031838 A1 | 3/2002 | Meinhart et al. |
| 2002/0036139 A1 | 3/2002 | Becker et al. |
| 2002/0070114 A1 | 6/2002 | Miles |
| 2002/0125138 A1 | 9/2002 | Medoro |
| 2002/0132316 A1 | 9/2002 | Wang et al. |
| 2003/0044832 A1 | 3/2003 | Blankenstein |
| 2003/0047456 A1 | 3/2003 | Medoro |
| 2003/0073110 A1 | 4/2003 | Aritomi et al. |
| 2004/0011652 A1 | 1/2004 | Bressler |
| 2004/0055891 A1 | 3/2004 | Pamula et al. |
| 2004/0058450 A1 | 3/2004 | Pamula et al. |
| 2004/0063196 A1 | 4/2004 | Muller et al. |
| 2004/0159546 A1 | 8/2004 | Zhang et al. |
| 2004/0191789 A1 | 9/2004 | Manaresi et al. |

(Continued)

FOREIGN PATENT DOCUMENTS

DE          3931851     4/1991
DE         19500660     6/1996

(Continued)

OTHER PUBLICATIONS

Petersson, Filip et al. "Carrier medium exchange through ultrasonic particle switching in microfluidic channels." Analytical Chemistry (2005) 77 1216-1221.*
International Search Report (PCT/IB2007/000751)—Aug. 21, 2007.
Altomare et al., Levitation and movement of human tumor cells using a printed circuit board device based on software-controlled dielectrophoresis, Biotechnol. Bioeng., 82(4):474-9 (2003).
Berthier et al., NSTI Nanotech 2005, vol. 1 (2005), www.nsti.org.
Bonci et al., The *miR-15a-miR-16-1* cluster controls prostate cancer by targeting multiple oncogenic activities, Nat. Med., 14:1271-7 (2008).

(Continued)

*Primary Examiner* — Christopher A Hixson
(74) *Attorney, Agent, or Firm* — Marshall, Gerstein & Borun LLP (57) ABSTRACT

Methods and apparatus are described for the processing (for example washing, incubation, etc.) of particles in which the particles suspended in a first fluid are introduced under laminar flow conditions into at least one first microchamber or first region of the same, in which a second fluid is introduced under laminar flow conditions into at least one second region of the microchamber or of a second microchamber, in such a way as not to mix with the first fluid, and in which at least one field of force acting on the particles is activated in the microchamber(s), to provoke a shift of the particles alone in a predetermined direction and to transfer the same in suspension into the second fluid; an apparatus is preferably used including at least three microchambers n microchambers arranged in sequence with each other in one direction and each connected with the microchamber immediately before it and after it with two orifices offset from each other in a direction perpendicular to the direction of sequence of the microchambers.

8 Claims, 3 Drawing Sheets

(56) References Cited

U.S. PATENT DOCUMENTS

| | | |
|---|---|---|
| 2004/0209354 A1 | 10/2004 | Mathies et al. |
| 2004/0229210 A1 | 11/2004 | Sabry et al. |
| 2005/0014146 A1 | 1/2005 | Manaresi et al. |
| 2005/0214736 A1 | 9/2005 | Childers et al. |
| 2006/0051775 A1 | 3/2006 | Bianchi |
| 2006/0086309 A1 | 4/2006 | Manger et al. |
| 2006/0139638 A1 | 6/2006 | Muller et al. |
| 2006/0177815 A1 | 8/2006 | Soh et al. |
| 2006/0223178 A1 | 10/2006 | Barber et al. |
| 2006/0228749 A1 | 10/2006 | Wang et al. |
| 2007/0026413 A1 | 2/2007 | Toner et al. |
| 2007/0026415 A1 | 2/2007 | Fuchs et al. |
| 2007/0051412 A1 | 3/2007 | Heath et al. |
| 2007/0059683 A1 | 3/2007 | Barber et al. |
| 2007/0172903 A1 | 7/2007 | Toner et al. |
| 2007/0250301 A1 | 10/2007 | Vaisberg et al. |
| 2008/0058991 A1 | 3/2008 | Lee et al. |
| 2008/0246489 A1 | 10/2008 | Coster et al. |
| 2008/0264068 A1 | 10/2008 | Nakasuka et al. |
| 2009/0205963 A1 | 8/2009 | Medoro et al. |
| 2009/0218223 A1 | 9/2009 | Manaresi et al. |
| 2010/0035292 A1 | 2/2010 | Levhenko et al. |
| 2010/0248285 A1 | 9/2010 | Manaresi |
| 2010/0331205 A1 | 12/2010 | Medoro |
| 2012/0071335 A1 | 3/2012 | Manaresi et al. |
| 2012/0091001 A1 | 4/2012 | Manaresi et al. |
| 2012/0184010 A1 | 7/2012 | Medoro et al. |
| 2013/0118903 A1 | 5/2013 | Becker et al. |

FOREIGN PATENT DOCUMENTS

| | | |
|---|---|---|
| DE | 10203636 | 8/2003 |
| EP | 1145766 | 10/2001 |
| EP | 1179585 | 2/2002 |
| EP | 1304388 | 4/2003 |
| JP | 58211272 | 12/1983 |
| JP | 2002311461 A | 10/2002 |
| JP | 2002536167 A | 10/2002 |
| JP | 2003121886 A | 4/2003 |
| JP | 2003202604 A | 7/2003 |
| JP | 2004000935 A | 1/2004 |
| JP | 2005501296 A | 1/2005 |
| JP | 2005507997 A | 3/2005 |
| JP | 2007017163 | 1/2007 |
| JP | 2008533487 A | 8/2008 |
| WO | WO-91/07660 | 5/1991 |
| WO | WO-91/08284 | 6/1991 |
| WO | WO-98/04355 | 2/1998 |
| WO | WO-99/17883 | 4/1999 |
| WO | WO-00/28313 | 5/2000 |
| WO | WO-00/47322 A2 | 8/2000 |
| WO | WO-00/69525 | 11/2000 |
| WO | WO-00/69565 | 11/2000 |
| WO | WO-02/12896 | 2/2002 |
| WO | WO-03/014739 | 2/2003 |
| WO | WO-03/035895 A2 | 5/2003 |
| WO | WO-03/045556 | 6/2003 |
| WO | WO-2004/030820 A2 | 4/2004 |
| WO | WO-2004/071668 | 8/2004 |
| WO | WO-2005/060432 | 7/2005 |
| WO | WO-2005/098395 | 10/2005 |
| WO | WO-2006/003214 | 1/2006 |
| WO | WO-2006008602 A2 | 1/2006 |
| WO | WO-2006/018849 | 2/2006 |
| WO | WO-2007/010367 | 1/2007 |
| WO | WO-2007/049103 | 5/2007 |
| WO | WO 2007/049120 | 5/2007 |
| WO | WO-2007/110739 | 10/2007 |
| WO | WO-2007/116312 | 10/2007 |
| WO | WO-2007/147018 | 12/2007 |
| WO | WO-2007/147076 | 12/2007 |
| WO | WO-2008/011274 A2 | 1/2008 |
| WO | WO-2008/131035 A2 | 10/2008 |
| WO | WO-2009/022222 A3 | 2/2009 |

OTHER PUBLICATIONS

Cheung et al., Impedance spectroscopy flow cytometry: on-chip label-free cell differentiation, Cytometry Part A, 65A(2):124-32 (2005).

Fiedler et al., Dielectrophoretic sorting of particles and cells in a microsystem, Anal. Chem., 80(9):1909-15 (1998).

Fiedler et al., Electrocasting formation and structuring of suspended microbodies using A.C. generated field cages, Microsystem Technologies, Berlin, Germany, pp. 1-7 (Dec. 1, 1995).

Final office action, U.S. Appl. No. 12/091,367, mail date Nov. 1, 2011.

Final office action, U.S. Appl. No. 11/724,697, mail date Jan. 27, 2012.

Fuchs et al., Electronic sorting and recovery of single live cells from microlitre sized samples, Lab Chip, 6:121-6 (2006).

Fuhr et al., Positioning and manipulation of cells and microparticles using miniturized electric field traps and travelling waves, Sensors and Materials, 7(2):131-46 (1995).

Gascoyne et al., Dielectrophoresis-based programmable fluidic processors, Lab Chip, 4:299-304 (2004).

Gascoyne et al., Particle separation by dielectrophoresis, Electrophoresis, 23(13): 1973-83 (2002).

Green et al., Ac Electrokinetics: a survey of sub-micrometre particle dynamics, J. Phys. D: Appl. Phys., 33:632-41 (Dec. 10, 1999).

Hughes, Strategies for dielectrophoretic separation in laboratory-on-a-chip systems, Electrophoresis, 23(16): 2569-82 (2002).

International Preliminary Report on Patentability for corresponding International Application No. PCT/EP2005/053235, mailing date Jan. 9, 2007.

International Preliminary Report on Patentability for corresponding International Application No. PCT/IB2009/007316, Jan. 21, 2011.

International Preliminary Report on Patentability for corresponding International Application No. PCT/IB2010/000615, dated Sep. 20, 2011.

International Preliminary Report on Patentability for PCT/IB2006/000636, dated Apr. 29, 2008.

International Preliminary Report on Patentability for PCT/IB2006/001984, dated Dec. 3, 2007.

International Preliminary Report on Patentability for PCT/IB2006/002965, dated Apr. 29, 2008.

International Preliminary Report on Patentability for PCT/IB2007/000751, dated Sep. 30, 2008.

International Search Report and Written Opinion for corresponding International Application No. PCT/EP2005/053235, mailing date May 2, 2006.

International Search Report and Written Opinion for corresponding International Application No. PCT/IB2009/007316, mailing date Feb. 3, 2010.

International Search Report and Written Opinion for PCT/IB2006/000636, dated Sep. 8, 2006.

International Search Report and Written Opinion for PCT/IB2006/001984, dated Feb. 27, 2007.

International Search Report and Written Opinion for PCT/IB2006/002965, dated Jun. 15, 2007.

International Search Report and Written Opinion for PCT/IB2010/000615, mailing date Aug. 26, 2010.

International Search Report in PCT/IB2008/002873, dated Aug. 3, 2009.

Jones, An electromechanical interpretation of electrowetting, J. Micromech. Microeng., 15(6):1184-7 (2005).

Klein et al., Comparative genomic hybridization, loss of heterozygosity, and DNA sequence analysis of single cells, Proc. Natl. Acad. Sci. USA, 96(8):4494-9 (1999).

Manaresi et al., A CMOS chip for individual cell manipulation and detection, IEEE Journal of Solid-State Circuits, 38 (12):2297-305 (2003).

Medoro et al., A lab-on-a-chip for cell detection and manipulation, IEEE Sensors Journal, 3(3):317-25 (2003).

Medoro et al., A lab-on-a-chip for cell separation based on the moving-cages approach, Proceedings of the 16th Conference on Solid State Transducers, pp. 500-501 (Sep. 15, 2002).

(56) References Cited

OTHER PUBLICATIONS

Medoro et al., Dielectrophoretic cage-speed separation of bio-particles, Sensors, Proceedings of the IEEE Vienna, Austria, Oct. 24-27, 2004, pp. 76-79.

Milner et al., Dielectrophoretic classification of bacteria using differential impedance measurements, Electronics Letters, 34(1):66-8 (1998).

Nagrath et al., Isolation of rare circulating tumour cells in cancer patients by microchip technology, Nature, 450(7173):1235-9 (2007).

Nieuwenhuis et al., Near-field optical sensors for particle shape measurements, Sensors Journal IEEE, 3(5):646-51 (2003).

Nonfinal office action, U.S. Appl. No. 11/724,697, notification date Jun. 7, 2011.

Nonfinal office action, U.S. Appl. No. 11/724,697, notification date Sep. 23, 2010.

Nonfinal office action, U.S. Appl. No. 11/996,068, mail date Jan. 4, 2013.

Nonfinal office action, U.S. Appl. No. 12/091,367, mail date Mar. 25, 2011.

Nonfinal office action, U.S. Appl. No. 12/091,438, mail date Jul. 25, 2013.

Nonfinal office action, U.S. Appl. No. 12/740,170, mail date Jun. 5, 2013.

O'Hara et al., Ratcheting electrophoresis microchip (REM) for programmable transport and separation of macromolecules, Proceedings of the International Mechanical Engineering Congress and Exposition, 3:619-28 (2001).

Office Action, U.S. Appl. No. 11,724,697, notification date Jan. 27, 2012.

Ohta et al., Tech. Dig. of the Solid State Sensor, Actuator and Microsystems, Workshop, pp. 216-219 (2004).

Petersson et al., Carrier medium exchange through ultrasonic particle switching in microfluidic channels, Anal. Chem., 77:1216-21 (2005).

Pethig et al., Enhancing traveling-wave dielectrophoresis with signal superposition, IEEE Eng. Med. Biol. Mag., 22(6):43-50 (2003).

Reichle et al., Combined laser tweezers and dielectric field cage for the analysis of receptor-ligand interactions on single cells, Electrophoresis, 22(2):272-82 (2001).

Romani et al., Capacitive sensor array for localization of bioparticles in CMOS lab-on-a-chip, Proc. Int. Solid State Circuit Conference, 1:224-5 (2004).

Rousselet et al., Directional motion of brownian particles induced by a periodic asymmetric potential, Nature, 370(6489):446-8 (1994).

Schnelle et al., Three-dimensional electric field traps for manipulation of cells—calculation and experimental verfication, Biochem. Biophys. Acta, 1157(2):127-40 (1993).

Stoecklein et al., Direct genetic analysis of single disseminated cancer cells for prediction of outcome and therapy selection in esophageal cancer, Cancer Cell, 13:441-53 (2008).

Suehiro, The dielectrophoretic movement and positioning of a biological cell using a three-dimensional grid electrode system, J. Phys. D: Appl. Phys., 31:3298-305 (1998).

Zieglschmid et al., Detection of disseminated tumor cells in peripheral blood, Crit. Rev. Clin. Lab. Sci., 42(2):155-96 (2005).

English translation of Office Action, Japanese patent application No. 2012-167396 (Aug. 2, 2013).

de Bono et al., Circulating tumor cells predict survival benefit from treatment in metastatic castration-resistant prostate cancer, Clin. Cancer Res., 14(19):6302-9 (2008).

\* cited by examiner

METHOD AND APPARATUS FOR THE PROCESSING AND/OR ANALYSIS AND/OR SELECTION OF PARTICLES, IN PARTICULAR BIOLOGICAL PARTICLES

CROSS REFERENCES TO RELATED APPLICATIONS

This application claims priority under all applicable laws and regulations to International Application PCT/IB2007/000751, published in English, filed on Mar. 26, 2007, designating the United States, which claims priority to Italian Application No. TO2006A000226, filed Mar. 27, 2006, each of which priority disclosures is incorporated herein by reference in its entirety.

TECHNICAL FIELD

The present invention concerns methods and miniaturised apparatus for the processing/manipulation of particles. The invention is applied principally in the implementation of biological protocols on cell samples in reduced volumes, as is often required by a miniaturised analysis approach.

STATE OF THE ART

In biology, the centrifuge is one of the instruments most used for the processing of cell samples, in particular with reference to certain stages of the process such as washing the cells. This is necessary for example when starting from a culture, for which it is desirable to remove the culture medium and re-suspend the cells in a saline solution, or when, after an incubation phase with antibodies and/or other reagents, one wants to wash away the excess antibodies and re-suspend the cells in a saline buffer, etc. The potential advantage that can be achieved with the reduction of the volumes involved has led to the miniaturisation of these stages of the process, which has stimulated the development of various methods of processing/manipulation.

In Seger et al. Cell immersion and cell dipping in microfluidic devices, LabChip, 2004, 4, 148-151, pressure-controlled liquid flows are used to exchange cells from one suspension buffer to another (washing), or to immerse cells originally present in a first buffer in a second buffer for a controlled time (incubation or reagent-sampling). The disadvantage of this approach is that it is necessary to maintain a controlled flow of the various liquids involved. This implies a greater consumption of reagents and a greater complexity of the system, linked with the necessity of producing pressure to flush (move) the liquids.

A similar approach is used by EVOTEC to submit single cells trapped in dielectrophoresis cages to particular reagents, but here too it is necessary to have controlled flows of reagents. The patent application PCT/WO 00/69565 a G. Medoro describes an apparatus and a method for the manipulation and identification of particles making use of closed cages with dielectrophoretic potential. The method described teaches how to control the position of each particle independently of all the others in a two-dimensional space. The force used to trap the particles in suspension is negative dielectrophoresis. The individual control of the manipulating operations is achieved by the programming of memory elements and circuits associated with each element of an array of electrodes and sensors integrated in the same substratum.

The U.S. Pat. No. 6,294,063 Becker et al. describes a method and apparatus for the manipulation of packages of solid, liquid or gaseous biological material by means of a distribution of programmable forces.

In the application for an Italian patent BO2005A000481, Medoro et al., some methods are given for manipulating particles with arrays of electrodes, and some methods and apparatus for identifying them, which are however similar to those of the already mentioned patent PCT/WO 00/69565.

Although it does not allow a precise control of the position of the particles, it is also possible to use Travelling Wave dielectrophoresis to shift the particles.

In other cases electrodes are not necessary to manipulate particles situated inside the microchambers.

Then there are many known methods of generating optical traps (optical traps, optical tweezers), which are based on the differences of the refraction index of the particles with respect to the suspension medium (for example A. Ashkin et al, Optical trapping and manipulation of single living cells using infrared laser beams, Nature, 330(6150) (1987) 769.)

In this case the particles are typically trapped in optical intensity maximums, generated for example by focussing a laser beam through the lens of a microscope. The manipulation of a multiplicity of particles may be obtained with various optical methods in the prior art, based on similar principles, for example using arrays of VCSEL (Vertical Cavity Surface Emitting Laser), or using holographic optical traps.

Other techniques are known, which combine the projection of images with luminous intensity gradients, the use of an electric field in the liquid and a device with a photosensitive substratum, to create so-called Opto-Electronic cages (for example U.S. Pat. No. 6,387,70781 assigned to Seul et Al., or Pei Yu Chiou et al, "Massively parallel manipulation of single cells and microparticles using optical images", Nature Vol 436, 21 Jul. 2005, pp 370-372). In practice a dielectrophoretic field is realised, controlled non by the shape of the electrodes but by the image projected on the photosensitive substratum. In this way it is therefore possible to manipulate the particles present in the liquid.

Lastly other techniques are known for moving particles. In S. Gaugiran, et al., "Optical manipulation of microparticles and cells on silicon nitride waveguides," Opt. Express 13, 6956-6963 (2005), some particles (artificial or biological such as yeasts and cells) are pushed along wave guides be the radiation pressure of the evanescent field of a laser which is spread inside the guide itself.

The international patent application in the name of the same Applicant, filed on 22 Mar. 2006 and concerning a method and an apparatus for making the characterisation and/or the count of particles of any type, for example biological particles such as cells or their parts, in which the control of the position of each particle present in a sample is used in order to shift those particles in a deterministic or statistical way, to detect their presence and/or characterise the type with optical integrated and/or impedenziometric sensors. In particular non uniform fields of force are used, variable times and optical or impedenziometric sensors located under or close to an array of electrodes, integrated with them in a single chip. The fields of force may have positive or negative dielectrophoresis, electrophoresis or electro-hydrodynamic movements, characterised by a set of stable points of equilibrium.

However, among the methods reported in the above-mentioned inventions concerning micromanipulators of cells/particles based on dielectrophoresis or other optical or optoelectronic techniques, although a flow is not necessary, no method is contemplated for allowing those typical operations such as washing and/or incubation of the cells or particles, as is necessary in many biological protocols.

SUMMARY OF THE INVENTION

The aim of the present invention is to supply a method and an apparatus for carrying out multiple operations typically performed, up till now, on a macroscopic scale with test tubes and centrifuges, performing them instead in a miniaturised way and/or with a lower consumption of reagents and/or a greater delicacy of action on the cells/particles and/or a greater efficiency of recovery of the processed cells and/or a greater control of the incubation/washing time and/or a greater automation and/or the extraction of particular information on individual cells.

Here and below, the terms "particles" or "particle" are used to indicate micrometric or nanometric entities, natural or artificial, such as cells, subcellular components, viruses, liposomes, niosomes, microbeads (microspheres) and nanobeads, or even smaller entities such as macro-molecules, proteins, DNA, RNA, etcetera, as well as drops of a fluid that cannot be mixed in a suspension medium, for example oil in water, or water in oil, or even drops of liquid in a gas (such as water in air) or, again, bubbles of gas in a liquid (such as air in water).

The term cell will sometimes be used, but where not specified otherwise it must be understood as a non limiting example of "particles" understood in the sense described more fully above.

According to the present invention, a method and an apparatus are therefore supplied for realising washing, incubation, and complex operations (for example marking of cells with antibodies and/or microspheres) as defined in the claims 1, 5, 9, 15, 16.

In particular non uniform fields of force are used, variable times and, optionally, integrated sensors, preferable of the optical type.

The fields of force may, for example, have positive or negative dielectrophoresis, electrophoresis or electro-hydrodynamic movements, characterised by a set of points of stable equilibrium for the particles (solid, liquid or gaseous).

In this way the limitations of the prior art are overcome by the present invention.

The implementation of the method according to the invention does not require pumps or flows of liquid generated otherwise.

Unlike centrifuges, the cells are subjected to lower stresses linked with the pressure exerted by the other cells in the pellet, or with friction with the walls of the test tube.

The method may be realised with miniaturised systems and the consumption of reagents may be drastically reduced, also because it is not necessary to support a flow of reagents.

Lastly, unlike the approaches that use flows to move the particles, by using a controlled field of force to move the particles from one buffer to the other it is possible to control precisely, one particle at a time, the time each of these remains exposed to each reagent.

Lastly the apparatus realised according to the invention allows the implementation of the method of the invention in a particularly advantageous way.

Further characteristics and advantages of the invention will be clear from the following description of some of its non limiting embodiments, with reference to the figures in the attached drawings.

DETAILED DESCRIPTION

The aim of the present invention is to supply a method and an apparatus for carrying out multiple operations typically performed on a macroscopic scale with test tubes and centrifuges, but performing them in such a way as to have one or more of the following advantages:
  miniaturisation;
  lower consumption of reagents;
  greater delicacy on the cells/particles;
  greater efficiency of recovery of the processed cells;
  greater control of the incubation/washing time;
  greater automation;
  integration of various steps of the process in a single integrated device;
  extraction of particular characteristic information on the individual cells (e.g. dynamics of reagent uptake, variations of volume, lysis) which are impossible with other methods.

The method of the invention is based on the use of a non uniform field of force (F) with which to attract single particles or groups of particles (BEADS) towards positions of stable equilibrium (CAGES). This field may be, as an illustrative example without limitation, a field of dielectrophoresis (DEP), negative (NDEP) or positive (PDEDP), or an electrophoretic field (EF), an optophoretic field, etc.

The identification of the effects on the particle resulting from its immersion in a second buffer may concern one of the following aspects, or combinations of the same:
  the identification of fluorescence
  the identification of absorbance, transmittance or other optical properties;
  the identification of variations of volume or other physical properties;
  the identification of impedenziometric properties;
  the identification of lysis of the particle.

Each of these observations may be carried out optionally at the level of a single cells, and with time resolution such as to appreciate the variation dynamics of the parameters studied.

Moreover, this information may be used not only to characterise the effects of the buffer on the particles, but to make a selective recovery of the particles with definite characteristics.

For this purpose the measurement of the impedance variation is principally used, and/or the measurement of the variation of light intensity, transmitted, diffused or emitted in fluorescence.

Generation of Forces

There are various methods for generating forces to shift particles, as described previously in the state of the art.

For the sake of simplicity, below is considered purely as an example, and therefore without limitation for the purposes of the present invention, the use of closed cages with negative dielectrophoresis as the activating force for the description of the methods and apparatus (for which it is necessary to use a cover acting as an electrode) of the invention. To experts of the sector with ordinary skills it is clear that is possible to generalise the methods and apparatus described below for the use of different activating forces, and different types of particles.

The common characteristics of the forces which allow particles to be manipulated according to the present invention is linked to the fact that these forces act mainly on the particle, moving the latter but not—or to a very limited extent—the liquid in which it is immersed.

The use of one or the other force is relevantly indifferent, unless fluorescent markers are involved. In these cases it is preferable to use forces based only on electric fields, so as not to cause photo-bleaching of the fluorophors, which could occur when applying the lighting otherwise necessary using optical or electro-optical methods.

Sensors Used

Also for the sake of simplicity, reference will be made below only to the case of optical sensors, which allow the measurement of the optical power acting on a photodiode integrated with the electrodes. To experts of the sector with ordinary skills it is clear that is possible to generalise, in the various cases, the methods and apparatus described below also for the alternative or combined use of integrated impedenziometric sensors.

It is also clear to the expert of the sector with ordinary skills in which cases the use of integrated sensors is beneficial and in which cases they are not necessary.

Method for Washing Particles

Figure 1:
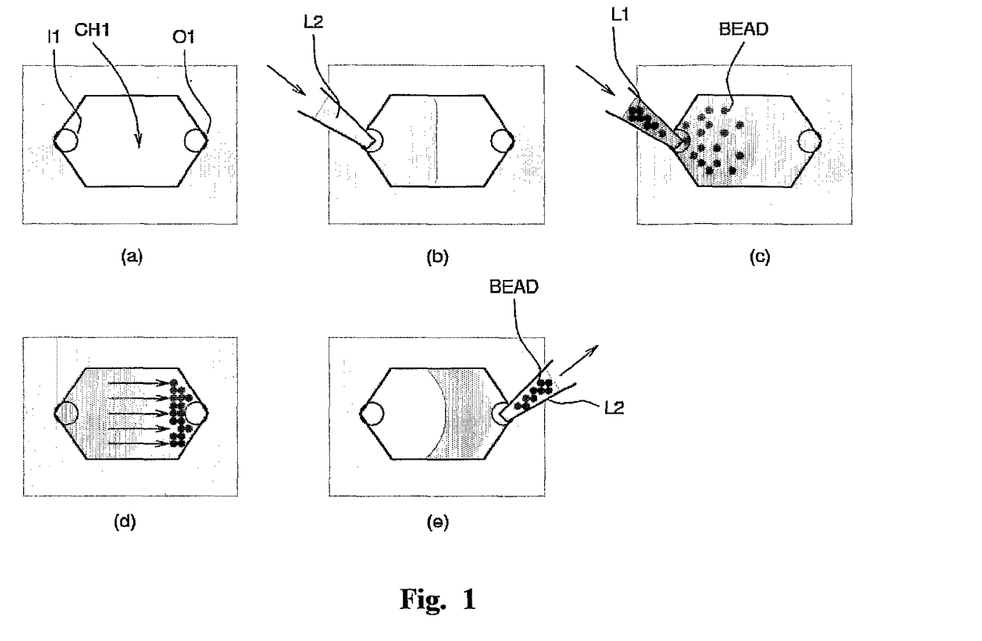
FIG. 1 shows an embodiment of a washing method realised according to the invention compatible with the use of forces acting on the particles in only one direction.
Figure 2:
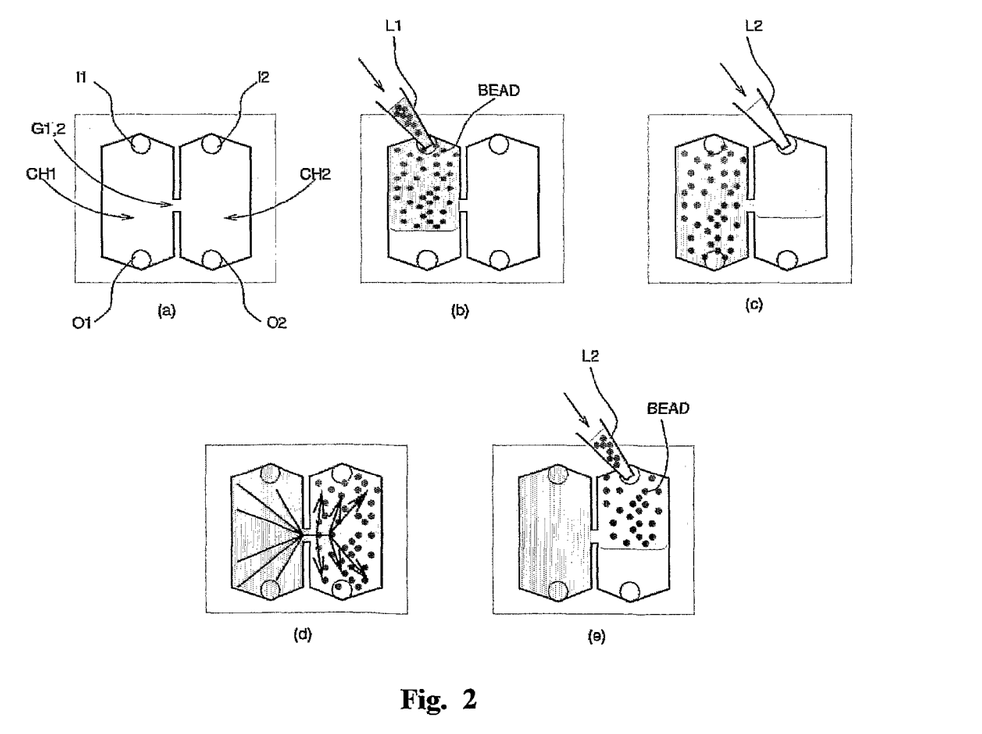
FIG. 2 shows an embodiment of a washing method according to the invention which requires the manipulation of particles in two dimensions.

Reference is made to FIG. 1 and FIG. 2.

The method exploits the fact that when two liquids (L1, L2), even of a type that generally mix together, are introduced into at least one microchamber (for example CH1, FIG. 1), in such a way as to realise a laminar flow for each liquid during the phase in which it is introduced into a predetermined region of the microchamber, the two liquids do not mix, apart from a very negligible mixing, for the purposes of the invention, being due to a slow process of diffusion, which process in any case begins only once the microchamber CH1 is filled and when a condition of stationary state has been reached in the two liquids.

As illustrated in FIG. 1, an apparatus is used including a single microchamber CH1 having an inlet orifice or input I1 and an outlet orifice or output O1 located at the opposite ends of the microchamber CH1, the floor or base of which, parallel to the plane of the sheet in FIG. 1, is composed of a substratum (chip) provided with an array of electrodes, eventually provided with sensors.

When the electrodes are energised, and the force (F) is activated which acts only on the particles (BEADS) present in suspension in the first liquid but leaves substantially immobile both the first and the second liquid, the particles (BEADS) are transferred (FIG. 1d) from the first liquid (L1) to the second (L2).

For example the first liquid could be a culture medium, and the second a physiological solution.

The operation may be repeated again, transferring the particles into further liquids (L3, . . . LN) in a way corresponding to multiple washing as usually carried out with test tubes and centrifuges.

However, with centrifuges the starting buffer is diluted in the destination buffer, for which reason it is often necessary to perform two or three washes so as to obtain a relative absence of the original liquid.

In the present invention, the contamination of the destination buffer (L2, . . . Ln) may be greatly limited if the movement of the particles (BEADS) is relatively rapid with respect to the times of diffusion of the molecules between the initial and the destination buffer. These diffusion times may be made relatively long with suitable stratagems, for example the one illustrated in FIG. 2, which shows the use, for the execution of the method of the invention, of an apparatus including two microchambers CH1, CH2, each provided with a floor having an array of electrodes that may be selectively energised and that are hydraulically connected to each other by a restriction or orifice G1,2 and each of which includes an inlet orifice or feed I1, I2, and an outlet orifice or discharge O1, O2, located at opposite ends of each microchamber CH1, CH2 and in a direction perpendicular to the one passing through the orifice G1,2.

While in the case of the apparatus in FIG. 2 the liquids L1 and L2 may be introduced in laminar movement in predetermined regions of the microchambers CH1, CH2 until the microchamber CH1 is totally filled with the liquid L1 and the microchamber CH2 with the liquid L2, then activating the electrodes so as to transfer the particles from the liquid L1 (and from the respective microchamber CH1) into the liquid L2 and the respective microchamber CH2, guiding them along the orifice G1,2, where there is the interface between the liquids L1, L2 which is small and therefore limits diffusive phenomena to a minimum, in the case of the apparatus in FIG. 1 it is first necessary to introduce the liquid L2 into the microchamber CH1, operating in laminar movement, through the orifice I1, without totally filling the microchamber CH1, but only a first region of the same (for example about half the volume of the microchamber CH1) situated close to I1 and, later, introduce through the same orifice I1 the liquid L1 with the suspended particles, still operating in laminar movement, so that the liquid L1 pushes the liquid L2 to occupy a second region of the microchamber CH1 situated near the outlet orifice O1, while the liquid L1 (with the suspended particles) occupies the first region of the microchamber CH1.

In any case, the particles suspended in the washing liquid L2 may be recovered by extracting the liquid L2 from the microchamber or region of the microchamber that it occupies, still working in laminar movement, through the orifice O1 (FIG. 1) or O2 (FIG. 2).

The method described substantially contemplates the phases of:

Introducing, in laminar flow conditions, first particles suspended in a first fluid (for example composed of a liquid, or a semi-liquid), into a first region of at least one microchamber.

Introducing, in laminar flow conditions, at least one second fluid (for example a liquid or a semi-liquid) into at least one second region of said at least one microchamber, so as not to mix said at least one second fluid with said at least one first fluid.

Activating in said at least one microchamber at least one field of force (F) acting on said particles, to provoke a shift of the particles alone towards said at least one second region of said at least one microchamber containing said at least one second fluid so as to suspend said particles in said second fluid.

Optionally (if no other process steps are necessary in the integrated device):

Selectively recovering said second fluid and said particles by extracting from said at least one microchamber said second fluid containing said suspended particles.

Method for the Incubation of Particles

Figure 3:
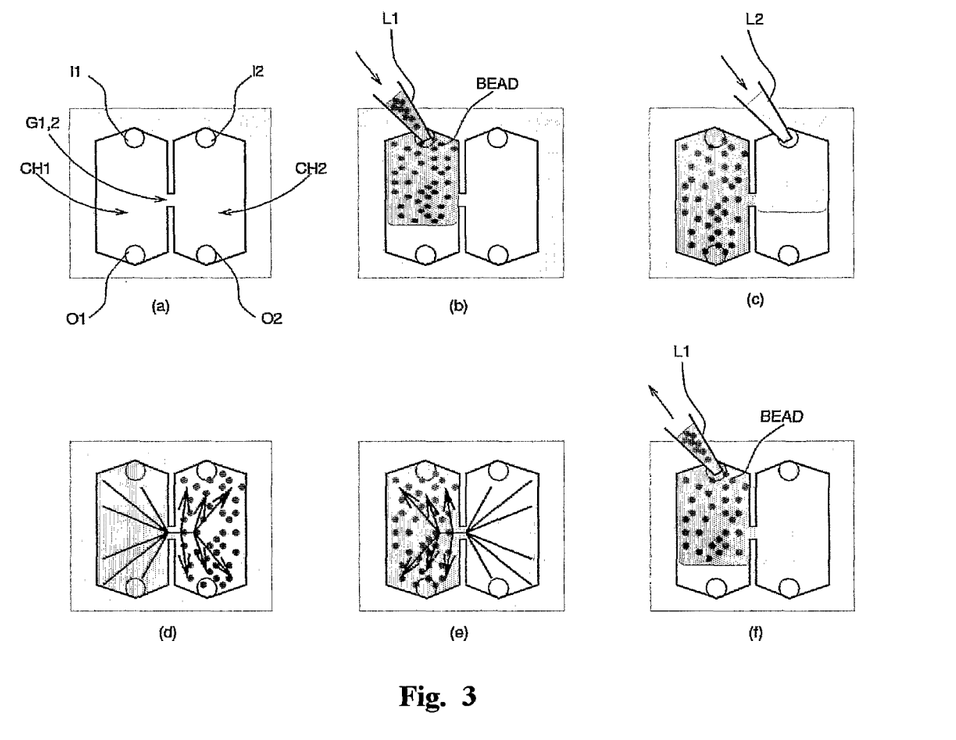
FIG. 3 shows an embodiment of a particle incubation method which requires the manipulation of particles in two dimensions.

Reference is made to FIG. 3.

In some ways the method is similar to the previous one, but it also contemplates the fact of returning the particles towards the starting buffer or towards a third destination buffer.

This is a typical problem linked with the process steps necessary for example to mark cells with antibodies (for example for membrane receptors) eventually coupled with microbeads (for example polystyrene particles) so as to immunodecorate the cells, with fluorescent tracing agents (for example intracellular dyes such as Calcein, FITC, acridine orange, Trypan Blue), or to fix cells (e.g. with paraformaldehyde), or to lysate certain cells selectively (e.g. exposing the cells to acetic acid, which lysates the red blood cells but not the leucocytes).

In these cases it is important not only to transfer the particles into a second liquid, but also to keep them in this second liquid for a definite length of time and then transfer them into a third liquid, which could also be the first (therefore returning the particles to the first liquid).

According to the present invention it is therefore possible to transfer the cells into a second liquid where they are exposed to suitable reagents, and then transfer them to a further liquid without reagents.

It is to be noted that, contrary to what can be done with test tubes and centrifuges, using the method of the invention it is possible to expose the particles to the reagent also for very short times.

In practice, the BEAD particles suspended in the first liquid (or general fluid) L1 (FIG. 3b) are introduced in laminar movement into a first microchamber CH1 of a manipulation apparatus of the type with two microchambers having the floor composed of arrays of addressable electrodes, hydraulically connected to each other by an orifice G1,2, identical to the apparatus illustrated in FIG. 2. Next (or simultaneously), operating in conditions of laminar movement, the general fluid or liquid L2 is introduced into the second microchamber CH2 (FIG. 3c) and the electrodes are then selectively activated to create a field acting with force F on the particles in such a way as to transfer them, through the orifice G1,2, from the microchamber CH1 to the microchamber CH2 without producing the shift of the liquids L1, L2 (FIG. 3d), which at this point are in stationary conditions; and then, after a predetermined incubation time (which may also be short as preferred), the particles are transferred by the force F back into the microchamber CH1 (FIG. 3e) which may still contain the starting liquid L1, or a new liquid (fluid) L3 ... Ln which in the meantime has been introduced into the microchamber CH1 through I1 after draining the liquid L1, for example through O1. Lastly the particles may be taken together with the liquid present in CH1 and in which they are suspended (FIG. 3f) through either O1 or I1, always operating in laminar movement.

The method described substantially contemplates the phases of:
Introducing, in laminar flow conditions, said particles suspended in a first fluid into a first region of at least one microchamber of an apparatus for manipulating particles;
Introducing, in laminar flow conditions, at least one second fluid into at least one second region of said at least one microchamber, so as not to mix said at least one second fluid with said at least one first fluid.
Activating in said at least one microchamber at least one field of force (F) acting on said particles, to provoke a shift of the particles alone in a predetermined direction into said at least one second region of said at least one microchamber containing said at least one second fluid, so as to suspend said particles in said second fluid;
Activating in said at least one microchamber at least one field of force (F) acting on said particles, to provoke a shift in the opposite direction to the previous one of the particles alone so as to bring them back into said at least one first region of said at least one microchamber.

Optionally, the method of the invention may also comprise the phases of:
Replacing said first fluid in said at least one first region of said at least one microchamber with at least one third fluid, before bringing said particles back into said at least one first region of said at least one microchamber;
Selectively recovering said particles by extracting from said at least one microchamber the fluid in which the particles are suspended.

Method for Carrying Out Complex Protocols

The washing and incubation operations may be composed in sequence, realising complex protocols. For example with the following phases:
1. Shifting the cells from the liquid Li to a different destination liquid Li+1
2. Waiting a period of time Ti+1
3. Shifting the cells from the liquid Li+1 to a further liquid Li+2
4. Repeating the preceding phases 2) and 3) until the cells or particles are suspended in a liquid Li+n.

For example the cells could be:
introduced suspended in the culture medium,
shifted into a region of the space occupied by a washing liquid (such as physiological solution),
transferred into a region of the space containing paraformaldehyde,
kept in this reagent for the time necessary to obtain the fixing and permeabilisation of the membrane,
washed by transferring them to a further region of the space containing physiological solution,
transferred into a region of the space containing proteins with fluorescent markers in order to recognise proteins potentially present inside the cell,
washed by transferring them to a further region of the space containing physiological solution,
analysed with sensors to recognise which cells express the proteins identified by the fluorescent marker.

According to this aspect of the invention, a method is therefore performed for carrying out complex experimental protocols on particles kept suspended in a fluid, comprising the phases of:
i) Suspending said particles in a first process fluid (Li) confined in a first region of space;
ii) Selectively shifting said particles into a second process fluid (Li+1) confined in a second region of space, maintaining the first fluid and the second fluid in stationary conditions, by applying to said particles a force F obtained by activating a field of force acting exclusively on said particles;
iii) Repeating phase ii) a number n of times until said particles are suspended in a final fluid (Li+n), so as to contact with said particles a plurality of different process fluids, at least some of which are able to interact with said particles;
iv) Analysing said particles with sensors located in a region of space containing said final fluid in a confined way.

Method for Studying the Dynamics of Reaction of Particles with Reagents

Contrary to what is possible also with techniques based on flow Microsystems such as the already mentioned Seger et al. LabChip, the time that the particles remain in the incubating reagent is not linked to the flow dynamics of the sample.

Moreover, every single particle may be exposed to the reagent for different times, even though it is manipulated in the same device. In fact it is sufficient to locate said particle in the region of space occupied by the reagent for a certain time Ti, and then bring it back into the final destination suspension buffer.

It is thus possible to expose N particles to a reagent for T1-TN different times.

It is therefore possible to study characteristics dynamically (with relation to time), such as for example the uptake of the reagent or the variation of characteristics that it causes on the cell.

This may occur with external optical sensors or preferably, using sensors integrated in the chip defining the floor of the microchambers CH1, . . . CHn used to keep confined the n process liquids with which to contact selectively the particles studied. The integrated sensor may be preferentially optical and/or impedenziometric. One may for example:

- Measure the uptake of a dye (for example trypan blue)
- Measure the uptake of a fluorochrome (for example FITC, acridine orange etc.)
- Measure the uptake of Calcein by increasing the fluorescence of a cell (Calcein is fluorescent only inside the cell);
- Measure the variation of volume of a cell;
- Check the lysis of a cell exposed to a reagent.

All this information can in fact be found in an integrated way according to the method of the prior art or, better, according to the methods described in the international patent application in the name of the same Applicant, previously mentioned.

This method, which is a variation of the one previously explained, therefore contemplates that the phases ii) and iii) described above are carried out in such a way as to expose a number N of particles to at least one predetermined reagent for T1, . . . TN different times; and that the phase iv) contemplates the dynamic study, with relation to time, of variable characteristics of said particles, such as for example the uptake of reagent or the variation of properties of the particles linked to reagent uptake.

Method for Studying the Secretion of Particles

Besides the characteristics of the cell, in terms of reagent uptake or the variation of physical properties, it is possible to study the secretion of single cells. To do this, the cells are moved towards a reaction buffer which contains substances that are modified depending on the presence of the type of molecules of which the secretion is to be studied.

If the secretion dynamics is sufficiently rapid with respect to the coefficient of diffusion of the secretion in the liquid, by analysing the liquid in the vicinity of the cell to be analysed with suitable sensors (for example optical sensors outside the chip defining the floor of the microchambers in which the reactions take place, or integrated in the chip, or impedenziometric sensors integrated in the chip), the cells that produce more or less secretion can be identified. In the prior art, numerous methods are available for revealing secreted substances. These methods may be used with few or no modifications in order to study the secretion, not of a group but, according to the invention, of single cells.

As an example without limitation, one may mention the use of chemiluminescent substances, of fluorescent substances with quenching which is inhibited by the presence of a certain secretion, or substances which change colour in the presence of a certain secretion.

If the diffusion of the secretion is too fast with respect to the dynamics of secretion and to the time scale for which the cells are to be analysed, it is necessary to adopt more elaborate solutions. Otherwise, the signal represented by the variation of colour, fluorescence, impedance or light intensity emitted, is not confined to an area around the cell and does not allow the separation of the signal coming from different cells.

In this case, the method comprises the phase of encapsulating the cells in porous/gelatinous substances which keep the secretion longer, slowing down its coefficient of diffusion and preventing the overlapping of the signal from different cells.

This method may be used for example in the selection of encapsulated cells to avoid rejection in transplants for therapeutic purposes.

The method just described therefore contemplates that the phases ii) and iii) described above are performed in such a way as to expose a predetermined number of particles, individually or in a group, to at least one predetermined reagent that is able to interact with any substances secreted by said particles; while phase iv) contemplates at this point the identification of this interaction with sensors, integrated or not. Moreover, it may optionally contemplate the phase of encapsulating at least some particles in porous/gelatinous substances able to keep back any substances secreted by the particles or at least to slow down their diffusion in the fluid in which the particles are suspended so as to prevent the overlapping of signals generated by the sensors in reply to the presence of different particles.

Method for Studying the Effects of the Exposure of Particles to Reagents

As well as the reaction dynamics, also the dynamics of the reactions of the exposure of a cell to a determined reagent may be analysed with high time resolution and above all with low delay.

By returning the single particles to a neutral buffer, the modifications generated by the exposure of the cells to the reagent may be studied after a variable period of time.

As above, this may be done with external optical sensors, or preferable with integrated optical or impedenziometric sensors.

For example one might want to check the expression of a reporter gene, or cellular differentiation.

Method for Selecting Particles

As well as observing the dynamics of reaction with a reagent, and observing the effects of the exposure to said reagent, it is possible to make an automatic selection of the cells based on the response of the same to the stimuli applied (in the form of reagents).

For example this allows the selection of the cells which, from a certain point of view, are more or less affected by a determined stimulus, or series of stimuli.

For example one might want to isolate the cells which absorb a smaller quantity of drugs of one type, or the cells that produce a greater quantity of a certain protein once exposed to a reagent.

So, according to this aspect of the invention, the phase is contemplated of selecting, in response to a signal detected by the sensors, the particles to which the generation of the signal is related; this selection phase is then carried out applying only to the particles related to the generation of that signal the force F generated by the field of forces that may be generated by means of the selective activation of the array of electrodes defining the floor of the microchambers to transport said particles and only them into a defined confined region of space, for example composed of a predetermined microchambers CHn or of a predetermined region of volume of the same microchamber in which the sensors are situated.

Method for "Constructing" Particles

By means of the methods described so far it is clear that one can also shift a particle or a group of "seed" particles from a first liquid to at least one second liquid, in which said particle(s) is(are) modified for example in one of the following ways: coating itself (for example with substances present in the second liquid or which are the product of the reaction between the particle and a reagent contained in the second liquid, growing (typically in the case of biological particles, such as cells, which may for example draw nourishment or a multiplication signal from the second liquid), soaking (typically in the case of artificial porous particles, such as microspheres).

The particle is then moved into a possible third, fourth, n-th reagent, realising a complex protocol to supply at the end "product" particles, for example composed of layers with controlled dimensions of different materials.

According to this aspect of the invention, a method is therefore provided for realising particles having a complex predetermined structure starting from first particles with a simple structure, comprising the phases of:

i) Suspending said first particles in a first process fluid (Li) confined in a first region of space;
ii) Selectively shifting said particles with a simple structure into a second process fluid (Li+1) confined in a second region of space, maintaining the first fluid and the second fluid in stationary conditions, by applying to said particles a force F obtained by activating a field of force acting exclusively on said particles;
iii) Repeating phase ii) a number n of times until said first particles are suspended in a final fluid (Li+n), so as to contact with said first particles a plurality of different process fluids, at least some of which are able to interact with said first particles in one of the ways chosen in the group comprising: coating, growing, soaking.

Apparatus for the Complex Processing of Particles

Figure 4:
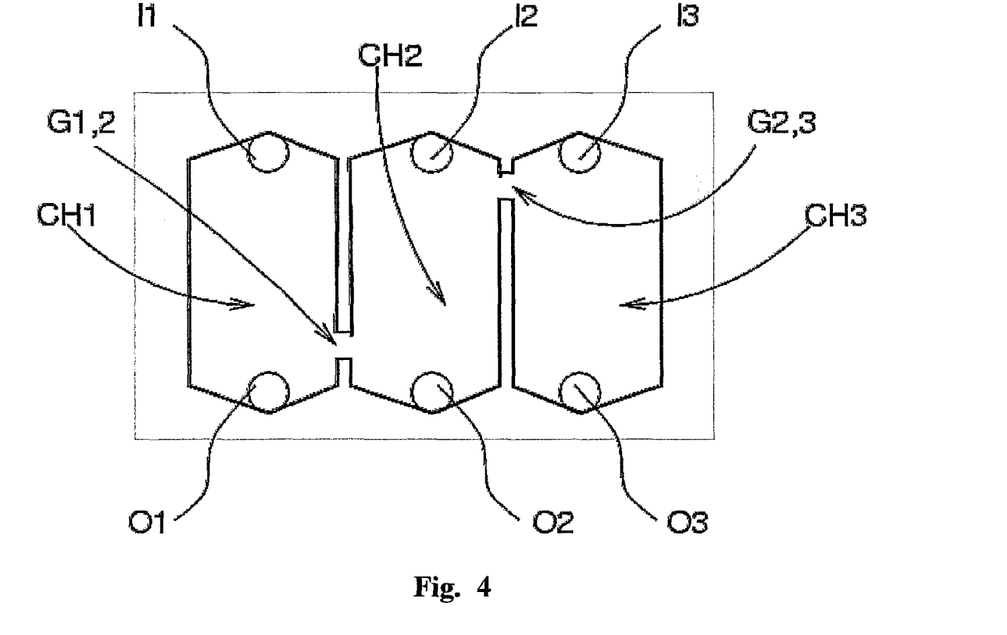
FIG. 4 shows a first apparatus realised according to the present invention.

In the case of multi-step protocols, which require a sequence of cell processing steps, it is particularly useful to realise a manipulating apparatus as schematically illustrated in FIG. 4, based on three microchambers CH1,CH2,CH3 arranged in sequence and realised as described previously for the microchambers CH1,CH2 in FIGS. 1-3, in which the central microchamber CH2 is hydraulically connected to the other two through two orifices G1,2 and G2,3 of hydraulic communication in the direction of the sequence of microchambers, which are located not only on opposite sides (in the direction of the sequence of microchambers) of the microchamber CH2, but are also offset to each other in the transverse sense, that is in a direction perpendicular to the direction of arrangement in sequence of the microchambers, being located one close to the inlet orifice I2 of the microchamber CH2 and the other close to the outlet orifice O2 of the microchamber CH2.

The central microchamber (CH2) is used for washing the cells between the buffer contained in the starting microchamber (CH1) and the reagent microchamber (CH3).

The first advantage of this device is that the distance between the orifices of hydraulic communication that constitute the two doors (G1,2) between the first and the second microchamber and (G2,3) between the second and the third microchamber increases the time necessary for the diffusion to contaminate the first starting liquid with the reagent in the third microchamber (CH3). Moreover, if after the passage of the cells washing buffer is flushed constantly into the second microchamber (CH2), any contamination between the reagent present in the third microchamber and the initial buffer is avoided.

Preferably, during flushing, the inlets and outlets (I1,I3 and O1,O3) of the other microchambers are kept closed, so as to keep the flow confined inside the second microchamber.

The liquids are preferably introduced in this order: CH1, CH3, CH2. In this way, as long as the meniscuses of the liquids L1 and L3 (that is the ones contained respectively in the microchambers CH1 and CH3) look onto the microchamber CH2, but do not touch, there is no contamination between the two due to diffusion.

Arbitrarily long multi-step reactions may be also be completed with this apparatus by completely replacing the buffer in the first microchamber (CH1) while the cells are in the third microchamber (CH3) and vice-versa. In this way the reagents are "multiplexed" in the space.

Alternatively a device may be realised in which all the reagents are injected in the initial phase and are already present at the start of the manipulation of the particles. This apparatus is shown in FIG. 5.

It comprises a first and a second terminal microchamber (CH1,CHn) and a plurality of intermediate microchambers (CH2, ... CHn−1) arranged in sequence between the terminal microchambers and each of which is hydraulically connected to the microchamber immediately before and immediately after in the direction of the sequence of microchambers by means of a respective first and second orifice (G1,2; Gn−1,n) of hydraulic communication in the direction of the sequence of microchambers, offset to each other in a transverse direction to the direction of the sequence of microchambers.

Figure 5:
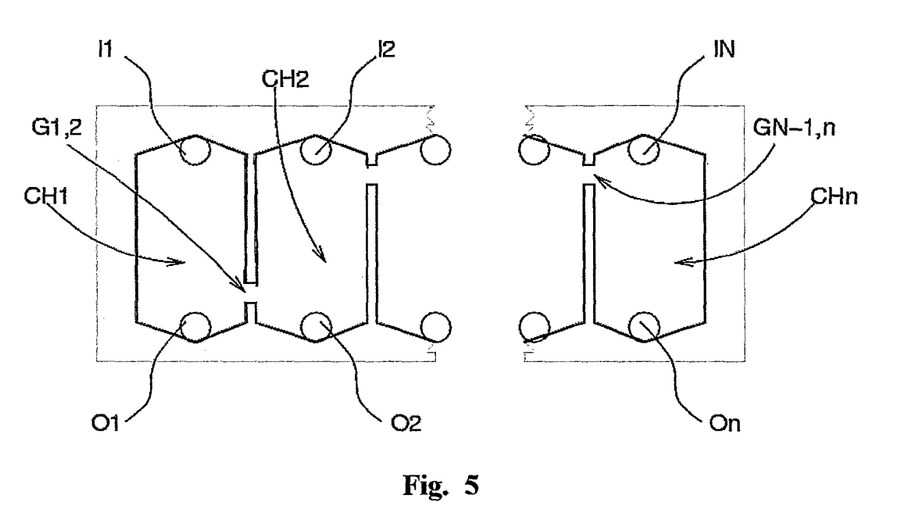
FIG. 5 shows a second apparatus realised according to the present invention.

Generalising what has been said previously, the apparatus in FIG. 5 is preferably filled firstly by filling the microchambers with an even index and secondly the microchambers with an odd index, so as to avoid contacts and contaminations until the liquids come into contact.

The invention claimed is:

1. A method for carrying out the washing of particles present in suspension in a first fluid by means of a second fluid, the method comprising:
   i) introducing said particles suspended in said first fluid into at least one microchamber of an apparatus for manipulating particles until a first region of the at least one microchamber is completely filled;
   ii) introducing at least one second fluid into said at least one microchamber until a second region of the at least one microchamber is completely filled, wherein the first fluid and the at least one second fluid are introduced into the at least one microchamber in laminar flow conditions such that the first fluid and the at least one second fluid do not mix during introduction into the microchamber and do not mix when both the first fluid and the second fluid reach a stationary state; and
   iii) activating in said at least one microchamber at least one non-uniform field of force acting on said particles to provoke a shift of one or more of the particles alone towards one or more points of stable equilibrium generated in said at least one second region of said at least one microchamber so as to suspend said particles in said second fluid, wherein the first fluid and the at least one second fluid are in a condition of stationary state when activating the at least one non-uniform field of force in the chamber, and the first fluid and the at least one second fluid remain substantially immobile during shifting of the particles, and the at least one microchamber is delimited by a plane or floor comprising an array of electrodes for activating the at least one non-uniform field of force.

2. The method according to claim 1, further comprising: selectively recovering said second fluid and said particles by extracting from said at least one microchamber said second fluid containing said suspended particles.

3. The method according to claim 1, wherein the first region of the at least one microchamber and the at least one second region of the at least one microchamber are first and second microchambers, respectively, connected to each other by a restriction or orifice of hydraulic communication between the microchambers, said first fluid being introduced into the first microchamber and said second fluid being introduced into the second microchamber.

4. The method according to claim 1, wherein a single microchamber is used, and wherein said second fluid being introduced first into the microchamber so that it occupies said second region of the microchamber only under the thrust of the first fluid which is introduced next into said first region of the microchamber.

5. A method for carrying out the incubation of particles present in suspension in a first fluid by contacting said particles with a second fluid, the method comprising:
   i) introducing said particles suspended in said first fluid into at least one microchamber of an apparatus for manipulating particles until a first region of the at least one microchamber is completely filled;
   ii) introducing at least one second fluid into said at least one microchamber until at least one second region of the at least one microchamber is completely filled, wherein the first fluid and the at least one second fluid are both introduced into the microchamber in laminar flow conditions such that the first fluid and the at least one second fluid do not mix during introduction into the chamber and do not mix when a condition of stationary state is reached in the first and the at least one second fluid;
   iii) activating in said at least one microchamber at least one non-uniform field of force acting on said particles to provoke a shift of one or more of the particles alone towards one or more points of stable equilibrium generated in said at least one second region of said at least one microchamber containing said at least one second fluid, so as to suspend said particles in said second fluid, wherein the first fluid and the at least one second fluid are in a condition of stationary state when activating in the at least one microchamber the at least one non-uniform field of force, and the first fluid and the at least one second fluid remain substantially immobile during shifting of the one or more of the particles; and
   iv) activating in said at least one microchamber at least one non-uniform field of force acting on said shifted particles, to provoke a shift of one or more of the shifted particles towards one or more points of stable equilibrium generated in said first region of said at least one microchamber, wherein the first fluid and the at least one second fluid are in a condition of stationary state when activating the at least one non-uniform field of force, and the first fluid and the at least one second fluid remain in the condition of stationary state when the shifted particles are shifted to the one or more points of stable equilibrium generated in the first region, and
   wherein the at least one microchamber is delimited by a plane or floor comprising an array of electrodes for activating the at least one non-uniform field of force.

6. The method according to claim 5, further comprising:
   replacing said first fluid in said at least one first region of said at least one microchamber with at least one third fluid, before bringing said particles back into said at least one first region of said at least one microchamber.

7. The method according to claim 5, comprising:
   selectively recovering said particles by extracting from said at least one microchamber the fluid in which the particles are suspended.

8. The method according to claim 5, wherein the first region of the at least one microchamber and the at least one second region of the at least one microchamber are first and second microchambers connected to each other by a restriction or orifice of hydraulic communication between the microchambers, said first fluid being introduced into the first microchamber and said second fluid being introduced into the second microchamber.

* * * * *

UNITED STATES PATENT AND TRADEMARK OFFICE
CERTIFICATE OF CORRECTION

PATENT NO. : 8,679,856 B2  Page 1 of 1
APPLICATION NO. : 12/294860
DATED : March 25, 2014
INVENTOR(S) : Nicolò Manaresi It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1134 days.

Signed and Sealed this

Twenty-ninth Day of September, 2015

Michelle K. Lee
*Director of the United States Patent and Trademark Office*